(12) United States Patent
Pryce Lewis et al.

(10) Patent No.: US 9,108,012 B2
(45) Date of Patent: *Aug. 18, 2015

(54) COATING METHODS AND COATED SYRINGE

(71) Applicant: GVD Corporation, Cambridge, MA (US)

(72) Inventors: Hilton G. Pryce Lewis, Lexington, MA (US); Neeta P. Bansal, Burlington, MA (US); Erik S. Handy, Malden, MA (US)

(73) Assignee: GVD Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/158,389

(22) Filed: Jan. 17, 2014

(65) Prior Publication Data

US 2014/0135708 A1    May 15, 2014

Related U.S. Application Data

(63) Continuation of application No. 12/605,011, filed on Oct. 23, 2009, now Pat. No. 8,668,972.

(60) Provisional application No. 61/108,342, filed on Oct. 24, 2008, provisional application No. 61/119,942, filed on Dec. 4, 2008.

(51) Int. Cl.
*A61M 5/315* (2006.01)
*B32B 1/00* (2006.01)
(Continued)

(52) U.S. Cl.
CPC .............. *A61M 15/009* (2013.01); *A61B 17/00* (2013.01); *A61L 29/085* (2013.01); *A61L 31/10* (2013.01); *A61M 5/3129* (2013.01); *A61M 5/31511* (2013.01); *A61M 5/31513* (2013.01); *A61M 25/0045* (2013.01); *B05D 1/60* (2013.01); *B05D 5/083* (2013.01); *A61B 2017/00526* (2013.01); *A61B 2017/00845* (2013.01); *A61L 2400/10* (2013.01); *A61L 2420/02* (2013.01); *A61L 2420/08* (2013.01); *A61M 15/00* (2013.01); *A61M 2005/3131* (2013.01); *A61M 2025/0046* (2013.01); *A61M 2205/0222* (2013.01);
(Continued)

(58) Field of Classification Search
CPC ........ A61L 31/10; A61M 3/00; A61M 5/178; A61M 5/31; A61M 5/31513; Y10T 428/1352; Y10T 428/1393
USPC .......... 428/34.1, 34.4, 34.6, 34.7, 34.9, 35.2, 428/35.4, 35.7, 36.4, 36.6–36.91; 604/19, 604/48, 93.01, 96.01, 187, 218, 222, 230, 604/265; 623/1.1, 11.11; 128/203.12, 128/203.15; 427/2.28
See application file for complete search history.

(56) References Cited

U.S. PATENT DOCUMENTS 5,380,557 A    1/1995    Spiro
5,888,591 A    3/1999    Gleason et al.
(Continued)

OTHER PUBLICATIONS

International Search Report & Written Opinion from PCT/US09/05780, mailed Jan. 7, 2010.

*Primary Examiner* — Walter B Aughenbaugh
(74) *Attorney, Agent, or Firm* — Pabst Patent Group LLP

(57) ABSTRACT

Medical articles with coatings are disclosed herein, as well as methods and systems for depositing these coatings onto medical articles. Surfaces of such articles may be coated. The coating(s) may serve as lubricants for reducing suction between such surfaces or between a coated surface and another surface.

18 Claims, 16 Drawing Sheets

(51) Int. Cl.
*B32B 1/08* (2006.01)
*A61M 15/00* (2006.01)
*A61B 17/00* (2006.01)
*A61L 29/08* (2006.01)
*A61L 31/10* (2006.01)
*A61M 5/31* (2006.01)
*A61M 25/00* (2006.01)
*B05D 1/00* (2006.01)
*B05D 5/08* (2006.01)

(52) U.S. Cl.
CPC ...... *A61M 2207/00* (2013.01); *Y10T 428/1352* (2015.01); *Y10T 428/1386* (2015.01); *Y10T 428/1393* (2015.01)

(56) References Cited

U.S. PATENT DOCUMENTS

| | | | |
|---|---|---|---|
| 6,090,081 A * | 7/2000 | Sudo et al. | 604/230 |
| 8,668,972 B2 * | 3/2014 | Lewis et al. | 428/35.7 |
| 2003/0031806 A1 * | 2/2003 | Jinks | 427/569 |
| 2005/0187466 A1 | 8/2005 | Glocker et al. | |
| 2007/0123920 A1 | 5/2007 | Inokuti et al. | |
| 2007/0235890 A1 | 10/2007 | Pryce Lewis et al. | |
| 2008/0071228 A1 * | 3/2008 | Wu et al. | 604/234 |
| 2009/0117268 A1 | 5/2009 | Pryce Lewis et al. | |

* cited by examiner

COATING METHODS AND COATED SYRINGE

RELATED APPLICATIONS

This application is a continuation of U.S. application Ser. No. 12/605,011, filed Oct. 23, 2009, now U.S. Pat. No. 8,668,972, which claims benefit of and priority to U.S. Provisional Application No. 61/108,342, filed Oct. 24, 2008 and U.S. Provisional Application No. 61/119,942, filed Dec. 4, 2008.

FIELD OF INVENTION

This invention relates generally to coated articles (e.g., medical articles), as well as methods and systems for forming the coatings.

BACKGROUND OF INVENTION

The interaction of medications with their storage vessels and delivery devices is attracting increasing attention. Such vessels and devices include glass vials (e.g., with rubber septa), glass or plastic syringes (e.g., with rubber-tipped plunger seals), and plastic metered-dose inhalers. For example, understanding the propensity of macromolecular protein-based pharmaceuticals to adsorb to storage vessel walls is of critical importance. If the adsorption rate is much greater than the desorption rate, the actual dosage of medication delivered to patients may be significantly lower than what was intended. In addition, it is often assumed that materials used for pharmaceutical storage are inert, i.e., unreactive and unchanging over the course of their service life. However, constituent chemical elements of these vessels (e.g., ions, solvents, surfactants, unreacted species) are known to leach out into liquid drug solutions and suspensions. The leachate itself may be harmful to the patient if administered with the drug. In addition, the leachate may perturb the pH, salinity, turbidity, etc. of the liquid drug. Such perturbations may have a dramatic impact on the biochemical activity of the drug (e.g., by changing the structure of pharmaceutical proteins), reducing the drug's efficacy or rendering it harmful.

Some medical articles are deliberately treated with lubricating surface coatings to improve their performance. For example, disposable, graduated syringe barrels may be siliconized to improve their lubricity. The sealing member attached to the drug-contacting syringe plunger tip may be surface-treated in the same way. Such lubrication facilitates sliding of the sealing member over the barrel's surface. This helps to ensure smooth delivery of the liquid drug stored in the syringe when the plunger is depressed. In addition to improving the convenience of using these syringes, lubrication prevents accidental administration of drug overdoses. A first surface which has been in contact with a second surface for a period of time must overcome stiction (static friction) in order to begin sliding over that second surface. Stiction between two surfaces is reportedly exacerbated by cold storage (as in a refrigerator). Syringe plungers and barrels are no exception. In order to start the plunger's sliding motion and push out the drug, one must initially apply more force than is later required to keep the plunger in motion. It may be difficult for medical personnel to determine exactly when different amounts of force are required during drug administration. Hence, the plunger may be pushed past its intended stopping point along the syringe barrel's graduations, resulting in an overdose. Lubricating coatings are intended to reduce both stiction and the expected dynamic friction once the sealing member is in motion.

Siliconization is a popular lubrication approach. That is, a small amount of liquid silicone oil (e.g., a low-molecular-weight polydimethylsiloxane) may be added to the syringe barrel surface or the sealing member surface, or both. Silicone oils have the advantages of chemical stability (being resistant to thermal and oxidative insult) and wide commercial availability, and the reputation for bio-inertness. For example, liquid silicones have been used extensively for anatomical enhancements, such as breast implants.

However, recent studies have cast doubt on some silicones' inertness. For example, silicone lubricants have been reported as encouraging the aggregation of proteins in solution, even at very low silicone concentrations. Insulin solutions have been reported to go increasingly turbid with prolonged exposure to silicone-lubricated syringes—a hallmark of macromolecular aggregation. These effects have disadvantages. The relationship between drugs and storage/administration devices preferably remains purely physical en route to the patient. Drug formulators generally want the confidence that their medications can be readily administered at the intended dosages, whether in dry powder, aerosol, or liquid form. Hence, there is a critical need for medical articles that preserve drug efficacy and safety during storage and administration.

SUMMARY OF INVENTION

Medical articles with coatings are disclosed herein, as well as methods and systems for depositing these coatings onto medical articles.

The medical articles may comprise a barrel and a seal, with the barrel having an inner surface coated with a polytetrafluoroethylene (PTFE) layer and the seal having an outer surface coated with a PTFE layer. The seal may be constructed and arranged to move from a first position to a second position within the barrel.

In one aspect, a method of coating medical articles with fluorocarbon is provided. The method comprises steps of dividing a vacuum vessel into a first zone and a second zone using a perforated plate; placing the medical articles in the perforations within the perforated plate separating the first zone from the second zone; evacuating the first zone such that a pressure differential is created between the first and second zones; adding a fluorocarbon vapor to the second zone; and forming a fluorocarbon coating may be formed on the medical articles as the fluorocarbon vapor moves from the second zone to the first zone.

In another aspect, a method of coating medical articles with fluorocarbon is provided. The method comprises steps of positioning medical articles in a vacuum vessel; evacuating the vacuum vessel using a first pumping system; evacuating the medical articles using a second pumping system; adding a fluorocarbon vapor to the vacuum vessel; and, forming a fluorocarbon coating on the medical articles as the fluorocarbon vapor moves through the medical articles into the second pumping system.

In another aspect, a method of coating medical articles with fluorocarbon is provided. The method comprises steps of positioning a the medical articles in a vacuum vessel; positioning a tube in the vicinity of the medical article chamber; evacuating the vacuum vessel; delivering a fluorocarbon vapor to the medical article chamber; and, forming a fluorocarbon coating on the medical article chamber.

In another aspect, a method of coating medical articles with fluorocarbon is provided. The method comprises steps of placing a substrate within a vacuum vessel; supporting the seals on pins protruding from the substrate; evacuating the vacuum vessel; adding a fluorocarbon vapor to the vacuum vessel; and, forming a fluorocarbon coating on the seals.

In another aspect, a method is provided. The method comprises generating reactive species by heating a gas with a filament, contacting the inner surface of a barrel with the reactive species to form a fluorocarbon layer, contacting the outer surface of a seal with the reactive species to form a fluorocarbon layer, and assembling the seal and the barrel to form a medical article constructed and arranged such that the seal can move from a first position to a second position within the barrel.

In some embodiments, only one of the inner surface of the barrel and the outer surface of the seal is contacted with reactive species to form a fluorocarbon layer.

Other aspects, embodiments and features of the invention will become apparent from the following detailed description of the invention when considered in conjunction with the claims.

DETAILED DESCRIPTION

Medical articles with coatings may ensure well-controlled delivery of medications to patients, such as through pre-filled syringes. A variety of medical articles may be suitable for use in connection with the embodiments described herein including syringe assemblies (including syringe barrels, plungers or pistons, and plunger seals or piston seals), drug cartridges, needleless injectors, liquid dispensing devices, liquid metering devices, metered dose inhalers and components thereof, dry powder inhalers and components thereof, catheters, and shunts. As described further below, surfaces of such articles may be coated. The coating(s) may serve as lubricants for reducing stiction between such surfaces (e.g., on disposable syringes) or between a coated surface and another surface. The coatings may also serve as inert surface treatments to discourage drug adsorption (e.g., for metered-dose inhalers, drug storage vials, and sealing stoppers for drug storage vials).

Figure 1:
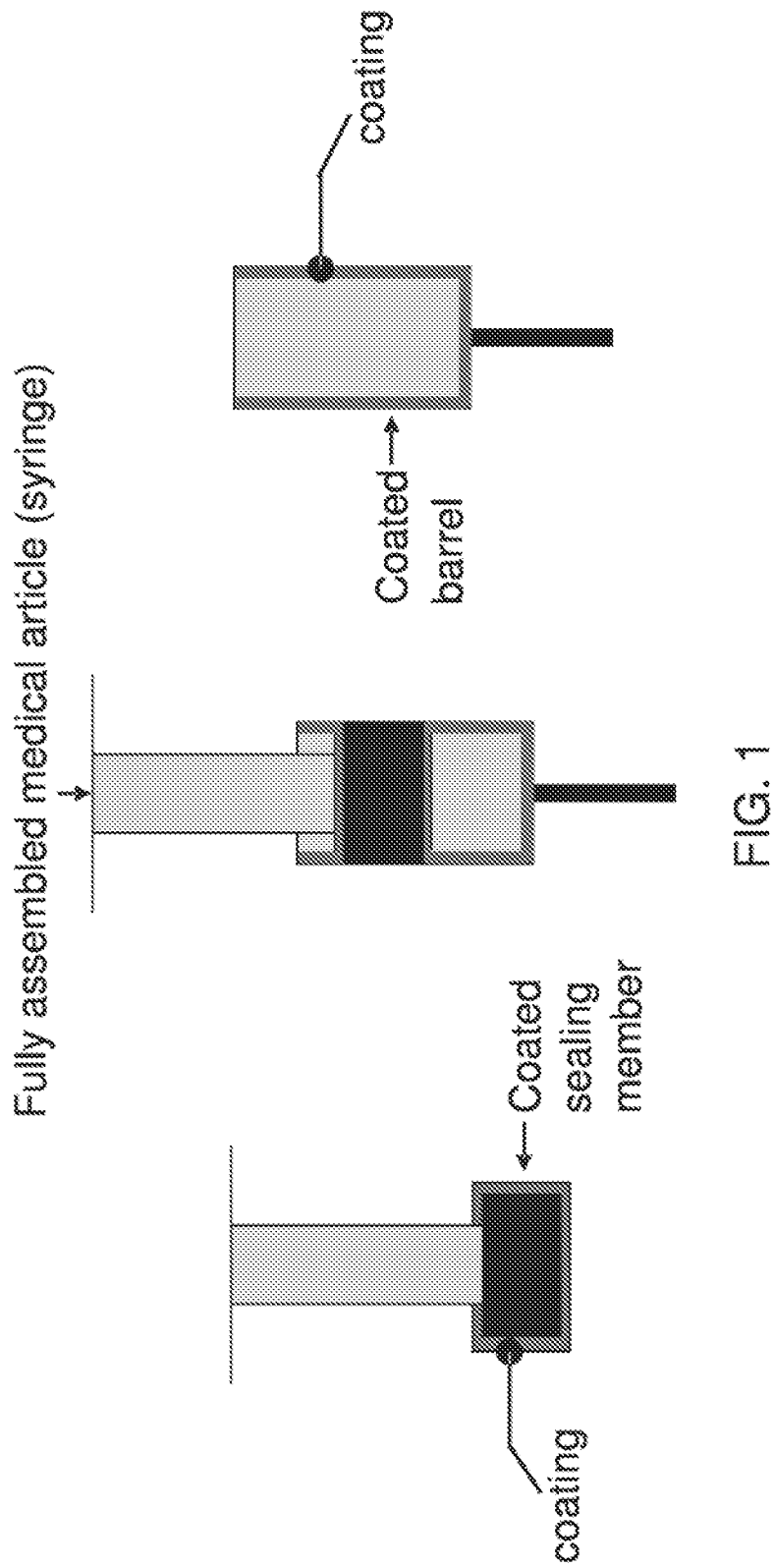
FIG. 1 shows a medical article according to an embodiment.

In some embodiments, the medical articles may include a chamber. The chamber can be a portion of a medical article in which materials are contained or through which materials pass. The chamber may be defined by a barrel (e.g., a syringe barrel) having an inner surface that includes a coating. An example of a chamber may be the internal volume of a syringe barrel (FIG. 1). Non-drug functional materials (such as an electrically-conductive epoxy, a contrasting imaging agent an or ink) may also be stored in and/or dispensed from the chamber of a syringe barrel.

In some embodiments, the medical articles include a seal. The seal may be in the form of a piston or plunger that moves from a first position to a second position within the barrel. The seal may contact a the surface of the barrel. In some embodiments, an outer surface of the seal may be coated. Seals or sealing members can join two mating surfaces together so as to keep materials from passing between the two surfaces. Examples of seals may include stoppers for vials or other storage vessels, or the tips of syringe plungers or syringe pistons that may be in contact with a drug stored in a syringe barrel, or O-rings. The seal may be made out of vulcanized rubber or a thermoplastic elastomer.

As shown in FIG. 1, the medical article may have a seal having its outer surface coated and a barrel having its inner surface coated. The coating(s) reduce the stiction as the seal moves from a first position within the barrel to a second position within the barrel. Such movement may result in dispensing a drug from the chamber of a syringe barrel.

In some embodiments, only one of the seal and the chamber includes a coating. In some embodiments, both the seal and the chamber include a coating.

Other suitable medical articles (such as a catheter or shunt) may have a barrel (or chamber) through which a piston or plunger may not pass, yet a drug may be stored in and/or dispensed from the chamber (also known as the lumen) of such articles. For example, drugs may pass through the chamber of a metered-dose inhaler or dry powder inhaler. Biological materials (e.g., blood, serum, lymph, saline solution, urine, semen, cerebrospinal fluid, synovial fluid, irrigation fluids, tissue samples, injectable hydrogels, etc.) may also be stored in and/or dispensed from the chamber of such articles.

Vessels for storing and/or dispensing non-drug materials (e.g. electrically-conductive, dielectric, or radiopaque inks, epoxies, or encapsulants which may be used in the construction or packaging of medical articles) may also be coated. Such materials may come in contact with biological materials (e.g., body tissue or fluids); hence, it may be important that they remain unadulterated by materials from their storage and/or dispensing vessels.

In some embodiments, the coatings comprise a fluorocarbon. Suitable fluorocarbons can include fluorinated hydrocarbon species such as fluorosurfactants, fluorinated monomers, fluorinated oligomers, fluorinated polymers, fluorinated copolymers, and fluorinated polymer blends. Examples of fluorinated polymers include fluorinated polyacrylates, fluorinated polyalkylacrylates, fluorinated polymethacrylates, fluorinated polyalkylmethacrylates, poly(vinyl fluoride), poly(vinylidene fluoride), and poly(tetrafluoroethylene). Poly(tetrafluoroethylene) is also referred to as PTFE, and sold commercially as Teflon®. In some embodiments, it may be preferred that the coatings comprise PTFE as described further below. PTFE coatings may be particularly well-suited to providing advantages to medical articles including increasing lubricity (e.g., by reducing coefficient of friction of article surface), reducing the adherence of chemicals on article surfaces, enhancing chemical resistance, and lowering surface energy of medical articles.

In some embodiments, the coatings (e.g., when the coatings comprise a PTFE layer) may also include a siloxane-containing layer. Siloxane-containing layers may be deposited onto the medical articles first, and then PTFE layers may be deposited on top of the siloxane-containing layers. These coatings may also prevent unwanted adsorption of drug molecules to the surfaces of medical articles. This performance feature is desirable because adsorption may alter the medication dosage that is delivered to the patient. These coatings may also prevent unwanted leaching of materials from the medical articles into the medications they contain. This performance feature is desirable because leaching may alter the performance of the medical article or the efficacy of the medication, or be harmful to the patient receiving the medication.

The siloxane-containing base layers that have an example atomic composition of C=42%, H=7%, O=19%, and Si=33%. The siloxane-containing base layers may improve the adhesion of fluorocarbon (e.g., PTFE) layers, as well as the fluorocarbon (e.g., PTFE) layers' resistance to abrasion. The siloxane-containing base layers may also improve the barrier properties of the coatings, which may reduce the leaching of materials from a medical article into the formulation that the medical article contains. Examples of siloxanes include polydimethylsiloxanes, polydialkylsiloxanes, poly(vinylsiloxane)s, and poly(vinylcyclosiloxane)s such as poly(trimethyltrivinylcyclotrisiloxane). That is, the siloxane units may be cyclic (such as ring structures).

The thickness of the fluorocarbon (e.g., PTFE) layer may range from about 1 nanometer to about 25 microns. In another embodiment, the thickness may range from about 5 nanometers to about 10 microns. In yet another embodiment, the thickness may range from about 25 nanometers to about 5 microns. The thickness of the siloxane-containing base layers may fall within the same ranges as the thickness of the PTFE layer.

As noted above, in some embodiments, the coatings include a PTFE layer. The molecular weight of the PTFE in the PTFE layer may range from about 138 g/mol to about 50,000 g/mol. PTFE with such a molecular weight may be produced using the iCVD (initiated chemical vapor deposition) process.

At least a portion of the PTFE layer may comprise PTFE polymeric chains having a high percentage of $CF_2$ repeat units (high chemical purity). For example, at least a portion of the PTFE layer may comprise polymeric chains in which at least 70% of the repeat units are $CF_2$. In some cases, at least 80% of the repeat units are $CF_2$; in some cases, at least 90% of the repeat units am $CF_2$; in some cases, at least 95% of the repeat units are $CF_2$; and in some cases, at least 99% of the repeat units are $CF_2$, or even about 100%.

This is notable in that typical plasma-enhanced chemical vapor deposition (PECVD) techniques often do not produce PTFE with such high chemical purity, with about 40-60% retention of $CF_2$ groups being more typical. Conventional PECVD PTFE coatings are often characterized by dangling bonds, double bonds, and crosslinks, PTFE layers formed on medical articles using conventional PECVD may therefore exhibit higher percentages of CF and $CF_3$ groups than the PTFE layers disclosed herein. The percentage of $CF_2$ units within the PTFE layer may be determined using magic angle spinning fluorine-19 magic angle spinning nuclear magnetic resonance ($^{19}$F-NMR) or high-resolution X-ray photoelectron spectroscopy (XPS).

The portion of the PTFE layer that comprises the high chemical purity PTFE chains may be the majority of the PTFE layer. For example, at least 50% (by weight) of the PTFE layer may comprise PTFE chains having the above-noted purities. In some cases, at least 75% (by weight), at least 80%, at least 90%, or substantially all of the PTFE layer may comprise PTFE chains having the above-noted purities.

However, it should be understood that other portions of the PTFE layer may not have the above-noted purities in some embodiments. For example, the portion of the PTFE layer that is initially deposited (e.g., closer to the medical article) may not have such high purities.

In some cases, the PTFE layers may exhibit a graded through-thickness oxygen content (e.g., increasing oxygen content closer to the medical article).

The PTFE layers disclosed herein may also be substantially free of polar end groups (such carboxylic acids, sulfonic acids, hydroxyl groups, amines, etc.). The PTFE layers disclosed herein may also be substantially free of non-PTFE contaminants, such as residual solvents and surfactants like perfluorooctanoic acid (PFOA). That is, PTFE layers may have high coating purity. PFOA and solvents may be used in conventional wet-applied PTFE dispersions as processing aids, and may thereby be incorporated into the resulting PTFE coatings. High-temperature drying (e.g., to remove solvents and surfactants), curing, annealing, sintering (e.g., to join individual PTFE particles used in the dispersion), etc. of conventional PTFE coatings may increase the cost and complexity of their use. (For example, plastic medical articles may not tolerate high-temperature processing.) Further, the gradual egress of any residual non-PTFE contaminants from conventional PTFE coatings may be undesirable, as this egress may change the properties of the PTFE coatings over time. In addition, when conventional PTFE coatings are used to coat medical articles, these contaminants may leach out of the PTFE coatings into the drug formulations or biological materials in contact with the medical articles, for example. PFOA is believed to be toxic (and possibly carcinogenic), and its use in and egress from conventional PTFE coatings at any stage of production may represent a health hazard.

The PTFE coatings disclosed herein may include parts-per-billion levels of metallic species (e.g., Ni, Cr, Cu, Sn, Fe, etc., possibly in any combination). Metal inclusion levels may be determined by liquid extraction followed by standard assays, which may include atomic absorption spectroscopic analysis.

Methods of the invention may be used to form fluorocarbons (e.g., PTFE) surface coatings on medical articles. The methods involve introducing a gas, or mixture of gases, into the vacuum vessel. The vacuum vessel may be evacuated using a vacuum pump(s) (e.g., to a pressure of several hundred millitorr) before the gas(es) is introduced. A metallic filament, such as one based on stainless steel, may also be resistively heated to a temperature of several hundred degrees Celsius before the gas(es) is introduced. For example, hexafluoropropylene oxide (HFPO) may be used as a gas in one embodiment of the invention. The gas(es) is heated to a desired temperature (e.g., several hundred degrees Celsius) and decomposes (i.e., pyrolyzes) into reactive species (e.g., radicals) that serve as monomer units. The units migrate to the article surface, which is at a lower temperature, where the units combine and grow into a coating having desired dimensions. A first gas may be introduced, followed by a second gas which is heated to the point of decomposition into reactive species. (For example, tertbutyl peroxide may be used as a second gas. The first gas and the second gas may also be introduced simultaneously.) The interaction of the first gas with the decomposed second gas may create a coating (e.g., a siloxane-containing coating deposited onto a medical article prior to a PTFE coating). It should be understood that the process parameters (e.g., feed gas composition, gas flow rate, total flow rate of fluorocarbon vapor through the medical articles, residence time of the fluorocarbon vapor, vacuum vessel pressure, heated filament temperature, medical article temperature, etc.) may be controlled to deposit a coating having the desired characteristics.

A method is disclosed comprising generating reactive species by heating a gas with a filament, contacting the inner surface of a barrel with the reactive species to form a fluorocarbon layer, contacting the outer surface of a seal with the reactive species to form a fluorocarbon layer; and assembling the seal and the barrel to form a medical article constructed and arranged such that the seal can move from a first position to a second position within the barrel.

FIGS. 2-7 illustrate different configurations of systems for coating articles.

Figure 2:
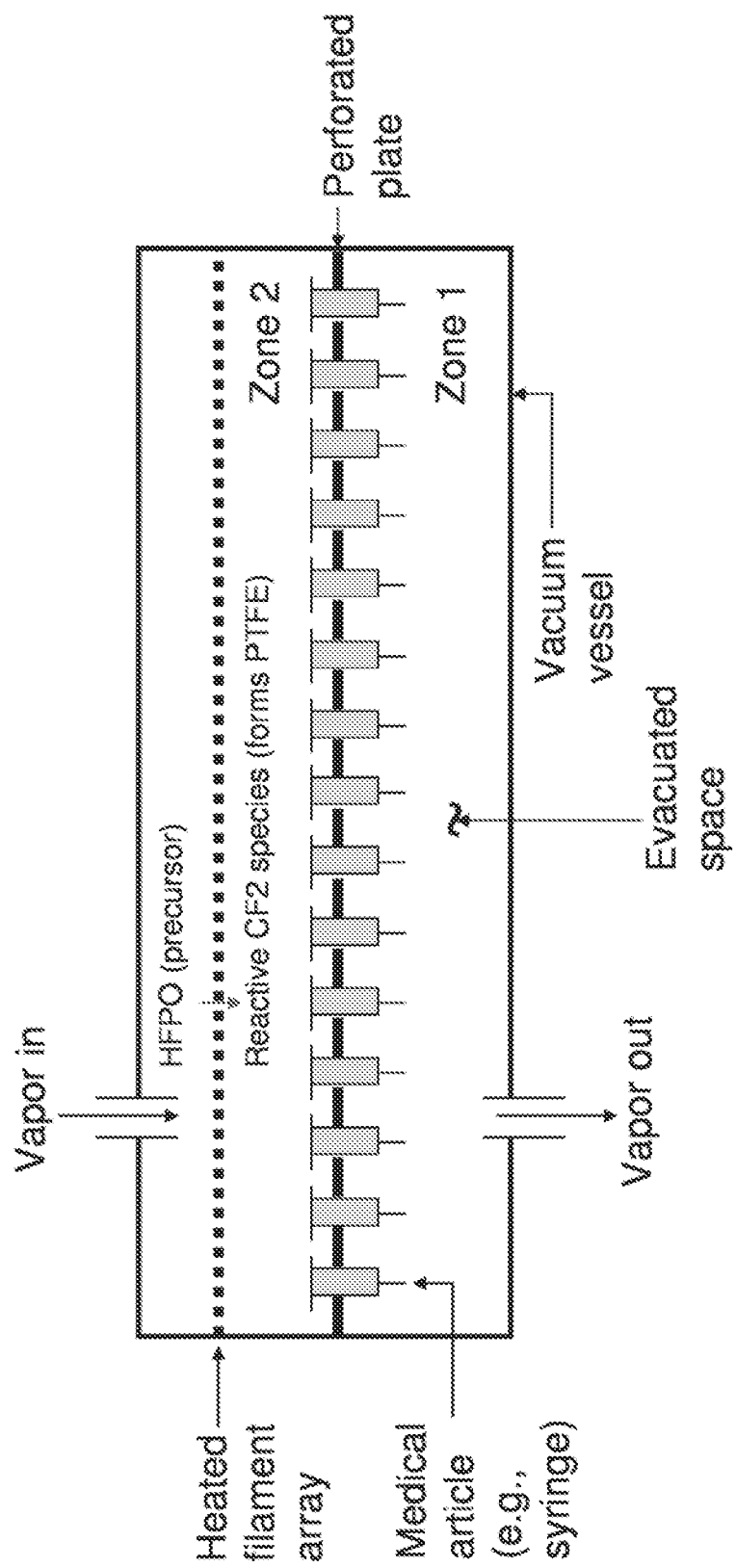
FIGS. 2-7 illustrate different configurations of systems for coating articles according to embodiments.

As shown in FIG. 2, medical articles (e.g., plastic syringe barrels) may be coated by dividing a vacuum vessel into a first zone and a second zone using a perforated plate; placing the medical articles in the perforations within the perforated plate separating the first zone from the second zone; evacuating the first zone (e.g., using a turbomolecular pump), such that a pressure differential is created between the first and second zones; adding a fluorocarbon vapor (e.g., HFPO) to the second zone; and forming a fluorocarbon coating (e.g., PTFE) on the medical articles as the fluorocarbon vapor moves from the second zone to the first zone. A pressure differential may be the difference in pressure between the first zone (which may be at a lower, first pressure) and the second zone (which may be at a higher, second pressure). The fluorocarbon vapor may be added to the second zone by pulsing. Pulsing may be achieved by opening and closing a bypass valve at the inlet where the fluorocarbon vapor enters the vacuum vessel, and/or between the first and second zones. The fluorocarbon vapor may be added in a direction that is substantially parallel or substantially perpendicular to the plane of the perforated plate. The perforated plate may be metallic, may be cooled (e.g., using circulating fluid cooled a refrigeration unit), and may be polished. The perforations in the perforated plate may contain rubber gaskets that may prevent the fluorocarbon vapor from passing from the second zone to the first zone through the perforations without forming a fluorocarbon coating on the medical articles. Medical articles may be attached to a metal retaining plate. A baffle may be placed in the vicinity of the medical articles to direct the fluorocarbon vapor towards the medical articles.

Figure 3:
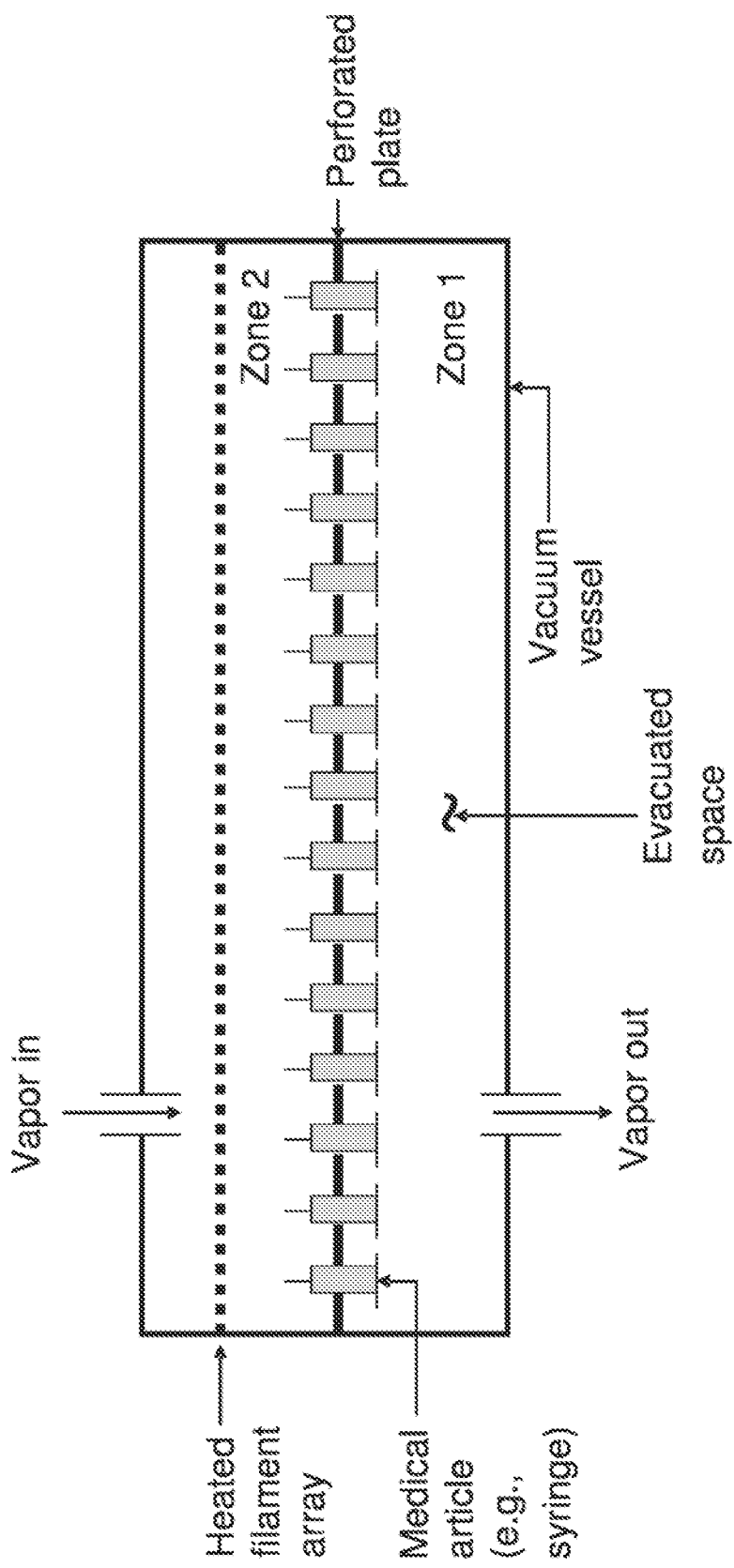
Figure 4:
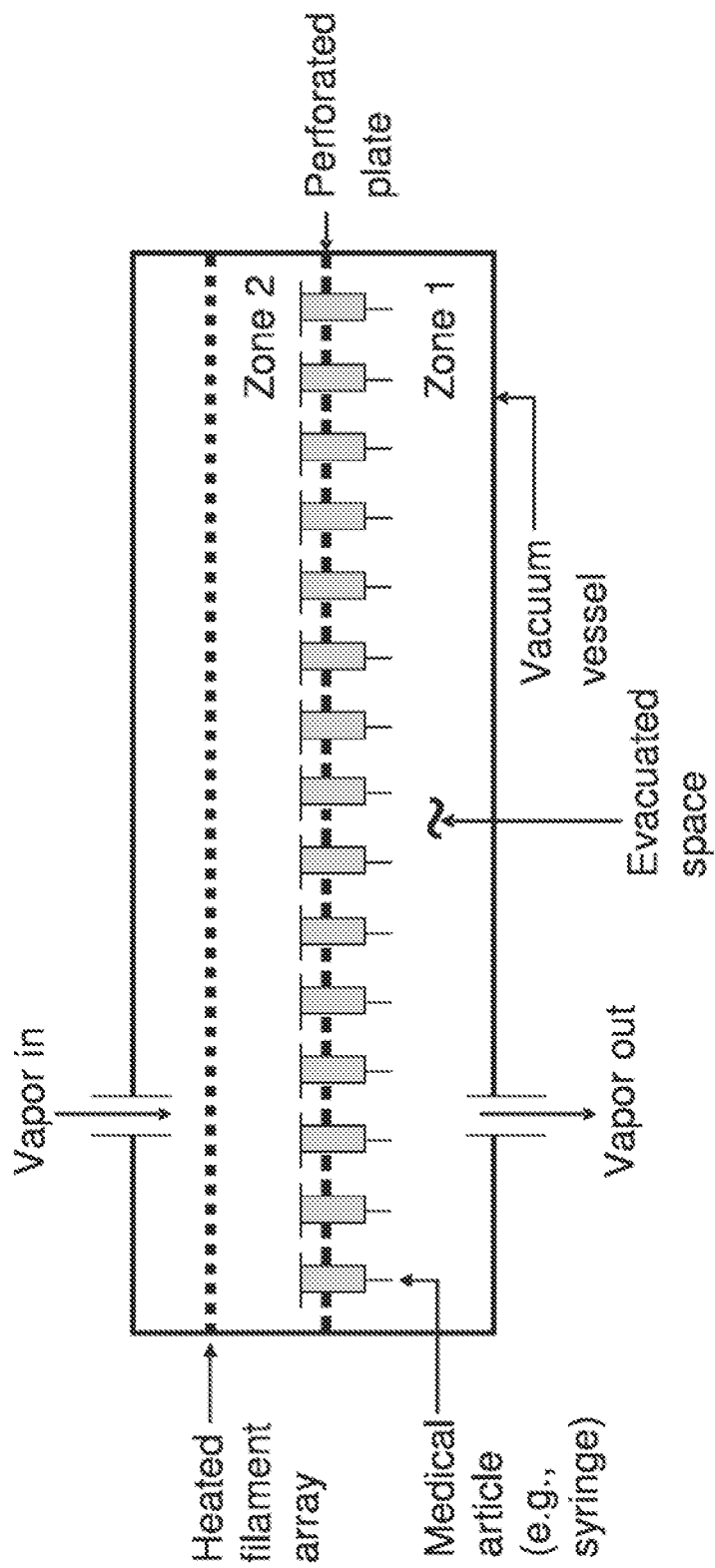

The medical articles may be placed in the perforations in a number of orientations. For example, medical articles having a barrel with a first internal diameter at a first end and a second internal diameter at a second end may be placed in the perforations such that the first end faces the first zone and the second end faces the second zone (FIG. 2). Alternatively, medical articles having a barrel with a first internal diameter at a first end and a second internal diameter at a second end are placed in the perforations such that the first end faces the second zone and the second end faces the first zone (FIG. 3). One of these medical article orientations may be preferred based on the coating being deposited, desired coating properties, pumping system(s) in use, and geometry of the medical articles being coated, for example. The pressure differential between the first zone and the second zone may be controlled. For example, additional perforations (bypass holes) may be created in the perforated plate so as to control the pressure differential, as shown in FIG. 4. These additional perforations may be useful for facilitating a desired coating deposition rate without compromising coating properties. For example, gas(es) may not pass from the second zone to the first zone at a desirable rate without additional perforations, causing the pressure differential to become too high. That is, the pressure in the second zone may increase due to input of fluorocarbon vapor (e.g., HFPO) and exceed desirable levels. As a result, a greater proportion of fluorocarbon (e.g., PTFE) formed by methods described herein may begin to form in the gas phase in the second zone prior to depositing on the medical articles. This may lead to the fluorocarbon (e.g., PTFE) coating on the medical articles having greater surface roughness and porosity than is desired for a given application. (Formation of PTFE or other fluorocarbon coatings on the surface of the medical articles may be preferable.) In the absence of additional perforations in the perforated plate, the rate at which fluorocarbon vapor is supplied to the second zone may have to be reduced in order to ensure that the fluorocarbon (e.g., PTFE) coating has the desired properties. A reduced fluorocarbon supply rate may reduce the overall coating formation rate, however, which may be undesirable from manufacturing and cost standpoints. If additional perforations are created, gas(es) may flow more easily from the second zone to the first zone, both preventing build-up of pressure in the second zone and facilitating a desirable coating deposition rate.

Figure 5:
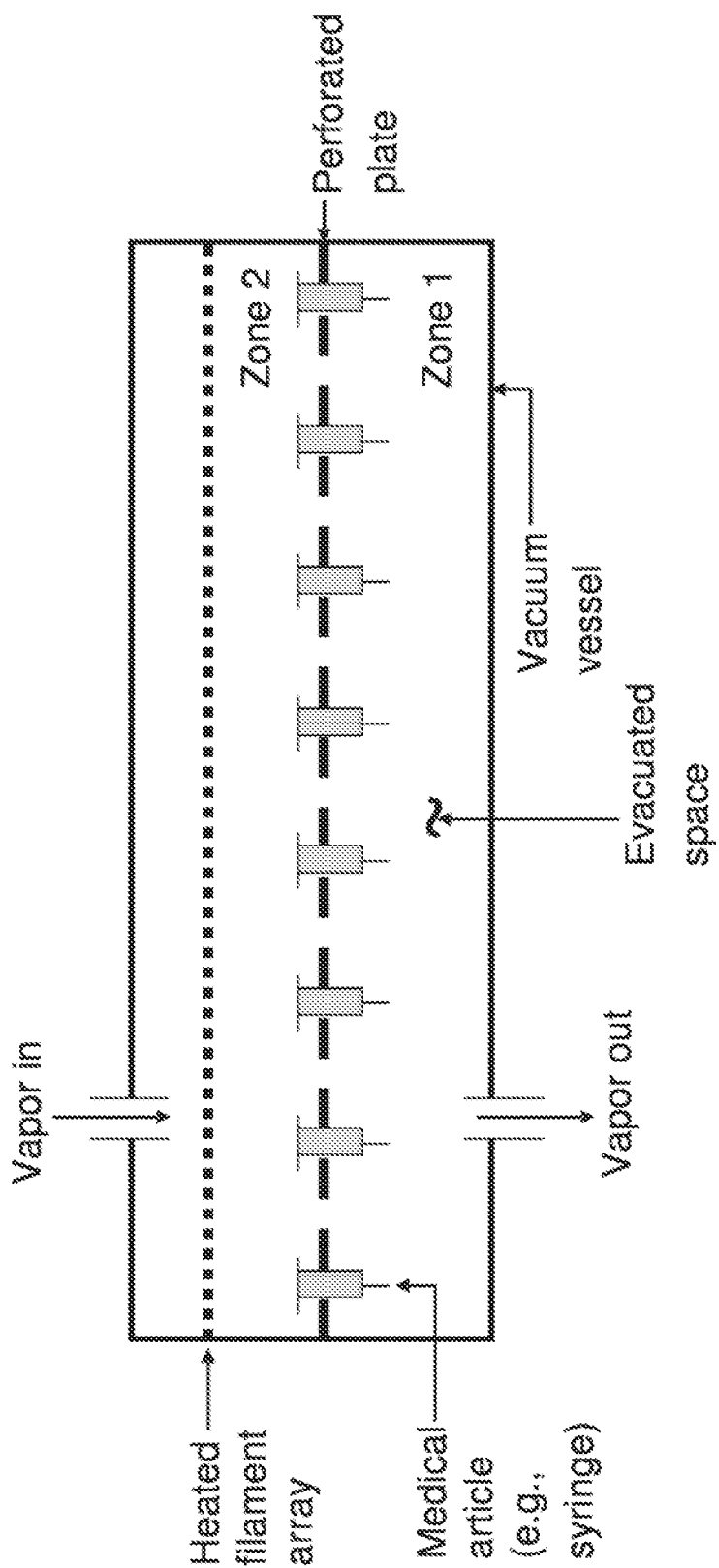

Alternatively, so as to control the pressure differential between the first zone and the second zone, perforations in the perforated plate may not have medical articles placed in them, as shown in FIG. 5. By leaving some of the original perforations open (and not populating them with medical articles), there may be no need to form additional perforations in the perforated plate. The pressure differential may also be controlled by making adjustments to a bypass duct between the first zone and the second zone. The pressure differential may also be controlled by adjusting the flow rate of fluorocarbon vapor added to the second zone (e.g., so as to keep the pressure in the second zone from rising to undesirable levels, as described above). The pressure differential may also be controlled by adding inert gas to the second zone. Adding inert gas may help increase the pressure differential between the second zone and the first zone (so as to encourage flow of reactive vapors through the medical articles). Because the inert gas is unreactive, however, it may not increase the proportion of fluorocarbon (e.g., PTFE) formed in the gas phase, for example. The pressure control methods may be focused on modifying the supply of gas to the second zone and modifying the rate at which gas may be allowed to leave the second zone. The pressure differential may also be controlled by adjusting the rate of evacuation of the first zone. That is, the pressure differential may be increased at a given second zone pressure, for example, by evacuating the first zone at a faster rate (e.g., with a turbomolecular pump).

For example, a fluorocarbon (e.g., PTFE) coating may be formed on syringe barrels using the iCVD (initiated chemical vapor deposition) process. In the iCVD process, a fluorinated precursor (such as HFPO) may be fed into the second zone of the vacuum vessel in the gas phase (FIG. 2). The HFPO may pass over resistively-heated filaments, which may cause the HFPO to decompose into reactive species, including difluorocarbene (:$CF_2$). The difluorocarbene species may then pass through the syringe barrels from the second zone into the first zone, forming a fluorocarbon (e.g., PTFE) coating on the syringe barrels. The gaseous effluent may then exit the vacuum vessel from the first zone.

Figure 6:
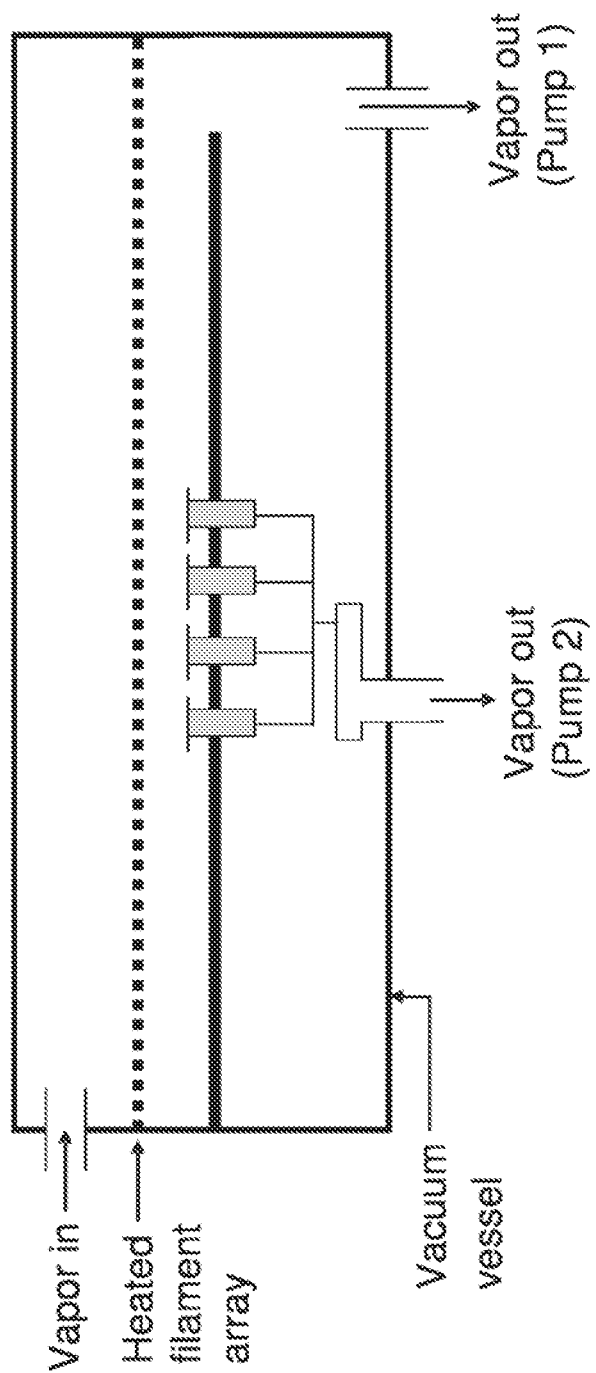
Figure 7:
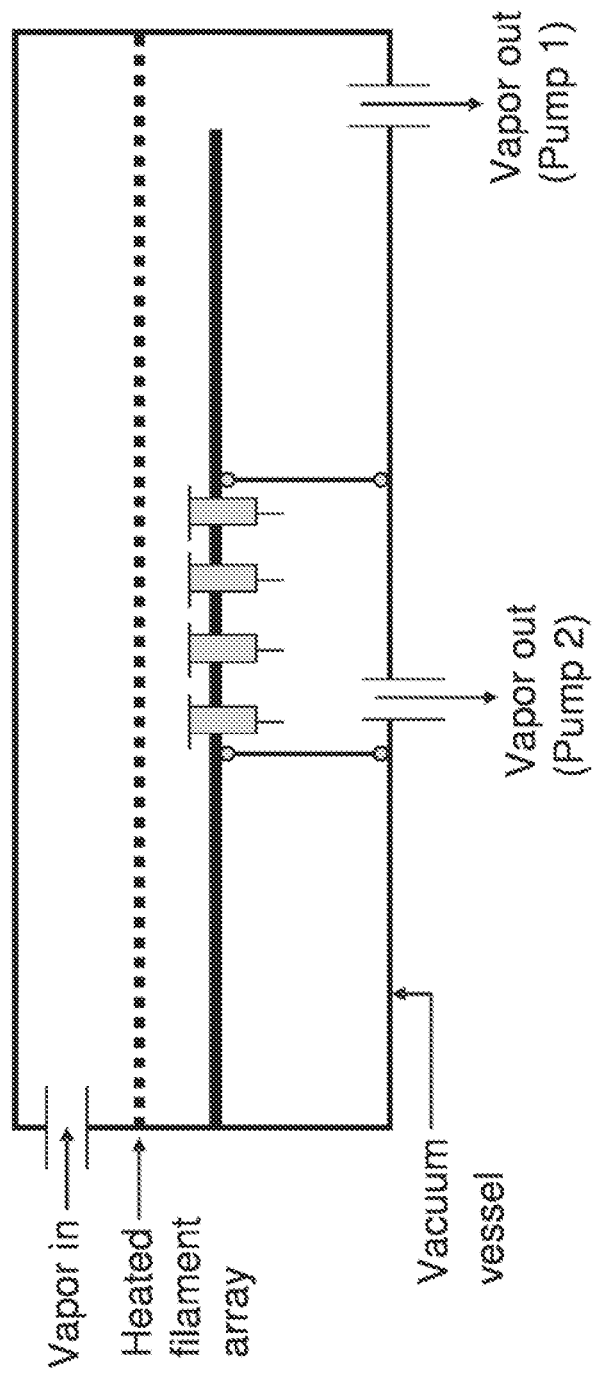

In another embodiment, medical articles may be coated by positioning the medical articles in a vacuum vessel; evacuating the vacuum vessel using a first pumping system; evacuating the medical articles using a second pumping system; adding a fluorocarbon vapor to the vacuum vessel; and forming a fluorocarbon coating on the medical articles as the fluorocarbon vapor moves through the medical articles into the second pumping system. The medical articles may be directly attached to a manifold using tubing, and the manifold and the tubing may be evacuated using the second pumping system (FIG. 6). The first pumping system may operate independently from the second pumping system. In this way, the second pumping system may evacuate each medical article individually, which may be desirable for some medical articles and some coatings. Alternatively, a second zone may be created around the medical articles, and the second zone may be evacuated using the second pumping system (FIG. 7). This approach may be simpler to follow (as it may require less labor), which may be desirable when a larger number of medical articles need to be coated in a short span of time.

Figure 8:
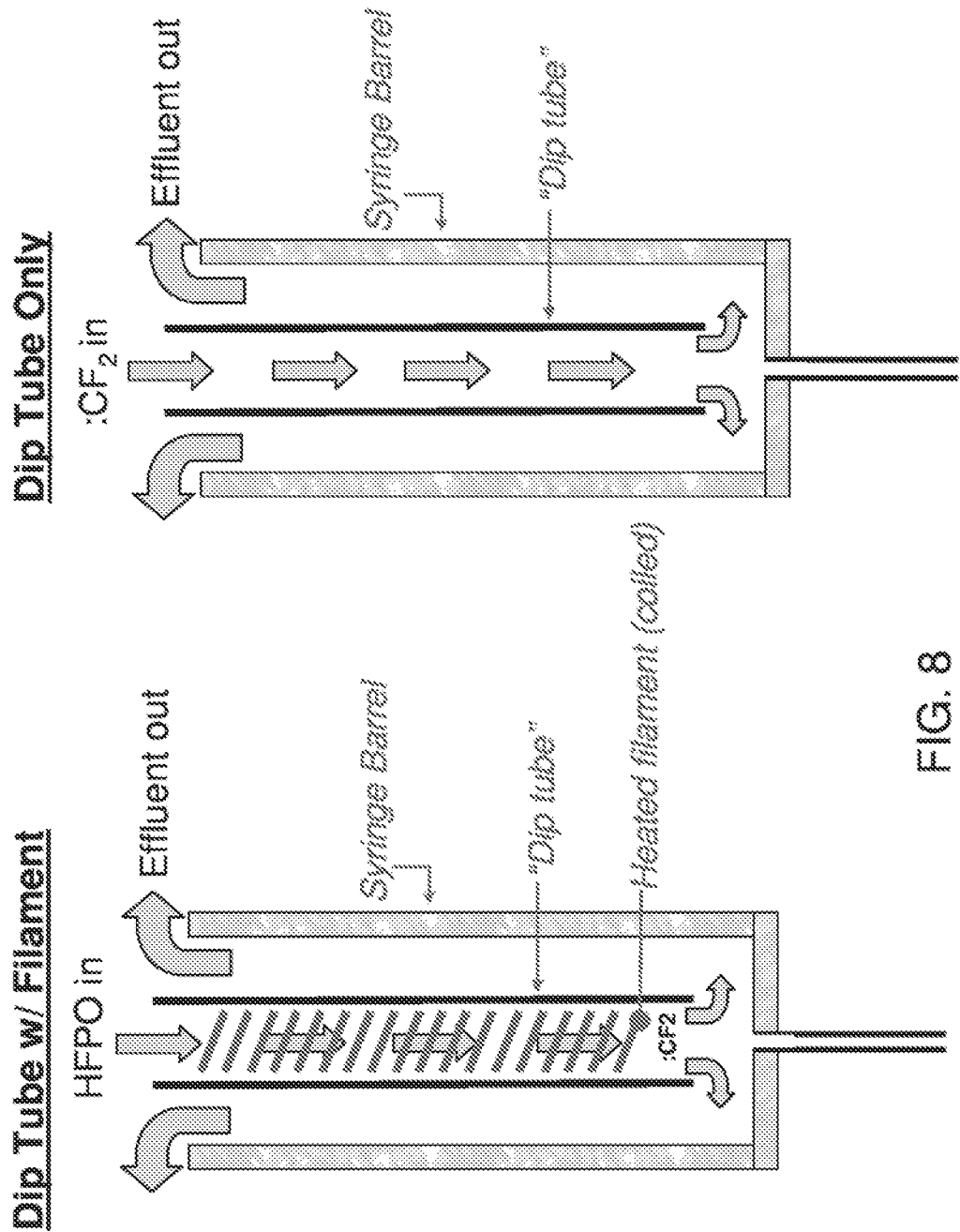
FIGS. 8-11 illustrate different configurations for coating a syringe barrel according to embodiments.
Figure 9:
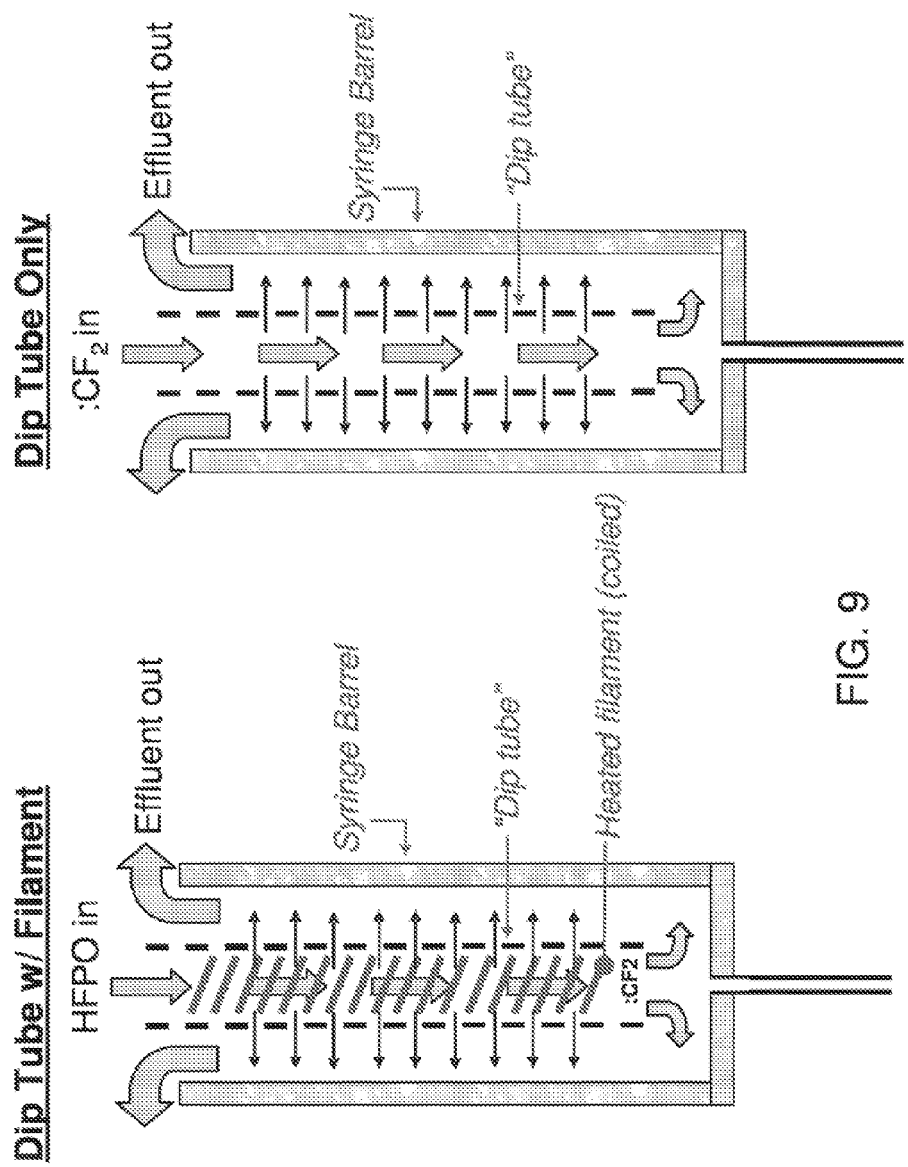

In another embodiment, medical articles may be coated by positioning the medical articles in a vacuum vessel, positioning a tube in the vicinity of the medical article chamber, evacuating the vacuum vessel, delivering fluorocarbon vapor to the medical article chamber, and forming a fluorocarbon coating on the medical article chamber. Fluorocarbon coatings may be formed on syringe barrels, for example, without the need for reactive vapors to pass completely through the syringe barrels. As shown in FIG. 8, reactive vapors may be directed toward the syringe barrel using a tube (positioned in the vicinity of the syringe barrel, e.g., within the barrel), which may encourage the formation of the coating on the syringe barrel. Specifically, the tube (e.g., a dip tube) may be inserted into the syringe barrel, and reactive vapors may then be fed into the barrel through the tube or evacuated from the barrel through the tube (FIGS. 8-11). As shown in FIGS. 8 and 9, the tube may contain a resistively-heated metal filament. The filament may be coiled. HFPO may be fed through the tube and over the heated filament, decomposing into difluorocarbene species that combine to form a PTFE coating on the syringe barrel. Alternatively, difluorocarbene species may be generated outside of the tube, then directed into the syringe barrel through the tube and form a PTFE coating on the syringe barrel (FIGS. 8-11). This may reduce the need to actively cool syringes placed in close proximity to any heated filaments. As shown in FIG. 9, the tube may be perforated.

Figure 10:
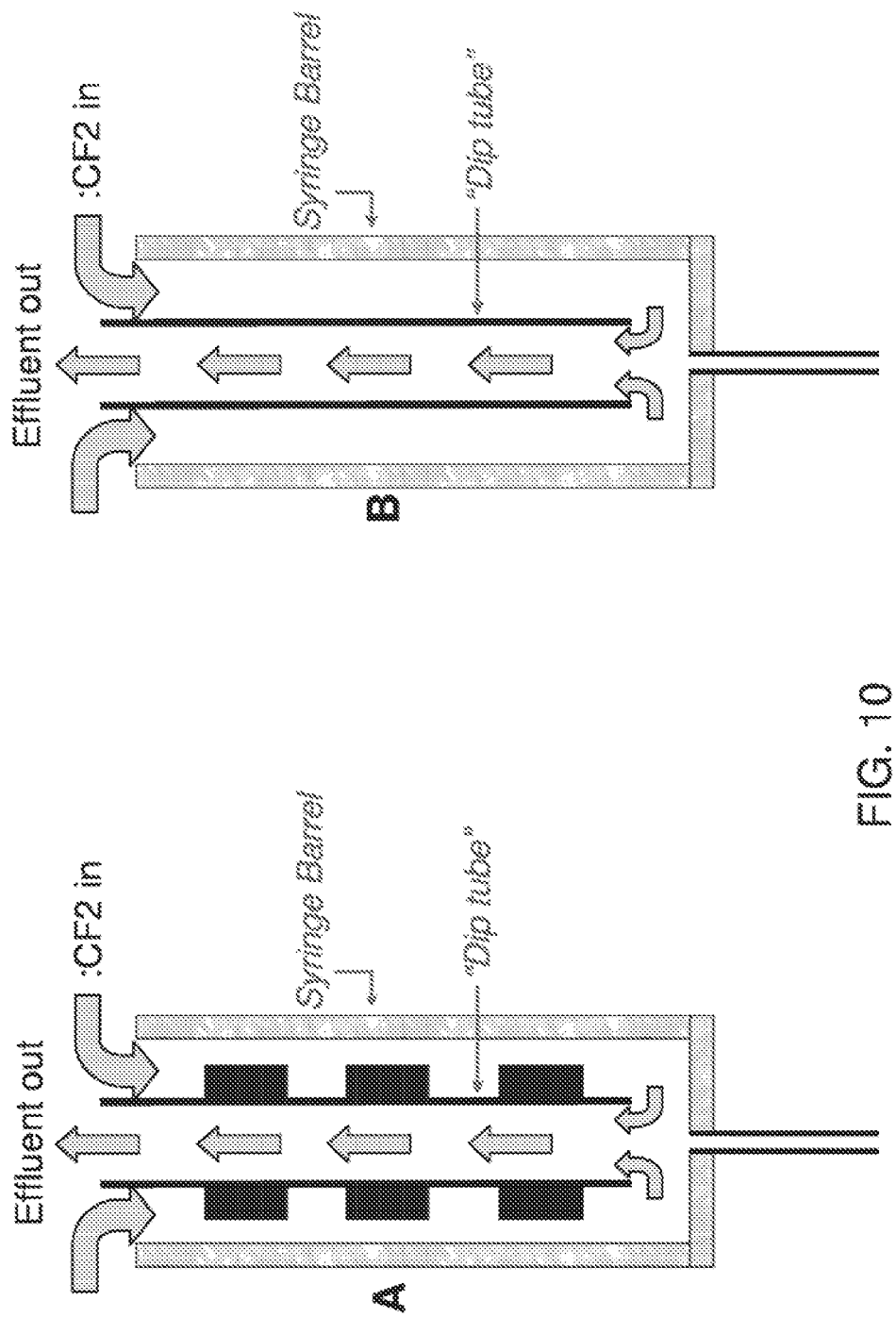
Figure 11:
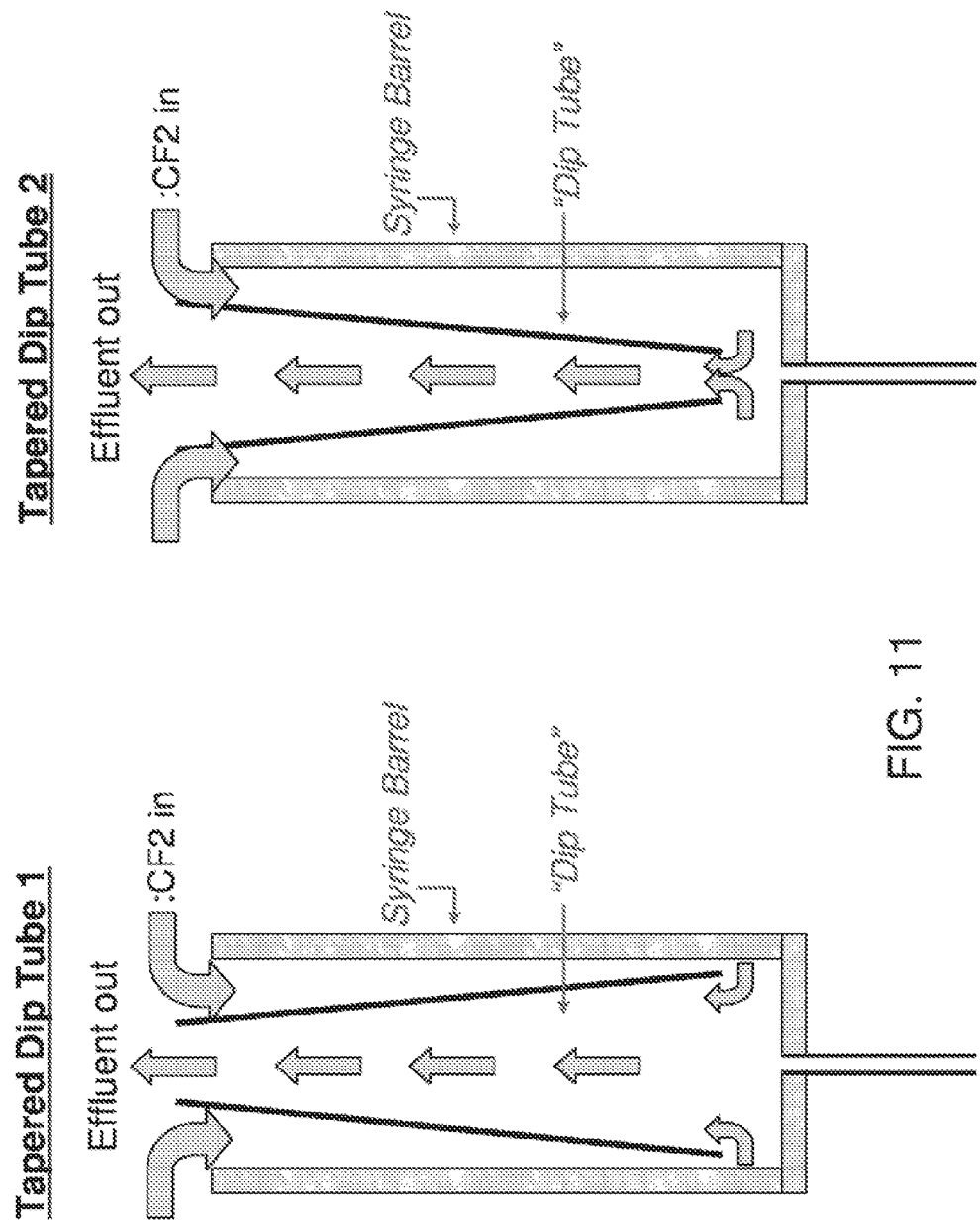

As mentioned above, fluorocarbon vapors (e.g., difluorocarbene species) may be generated elsewhere in the vacuum vessel. Heated metal filaments may be used to activate the fluorocarbon vapor (e.g., by pyrolysis and/or by pyrolysis of an initiator vapor). Fluorocarbon vapors may be drawn into the medical article (e.g., delivered to the chamber of a medical article, such as the barrel of a syringe) by evacuating the tube. Irrespective of where the reactive vapors are formed, the tube may have a shape that is non-cylindrical. As shown in FIGS. 10 and 11, the tube may be tapered, crenelated, notched, or screw-shaped, for example, A notched, crenelated, or screw-shaped tube may create additional turbulence in the flow of vapor onto (or into) the syringe barrel, and such turbulence may encourage coating formation on the syringe barrel. A tapered tube may change the velocity of the flow of vapor onto (or into) the syringe barrel and the spacing between the outer tube wall and the inner syringe barrel wall, which may also encourage coating formation on the syringe barrel.

Figure 12:
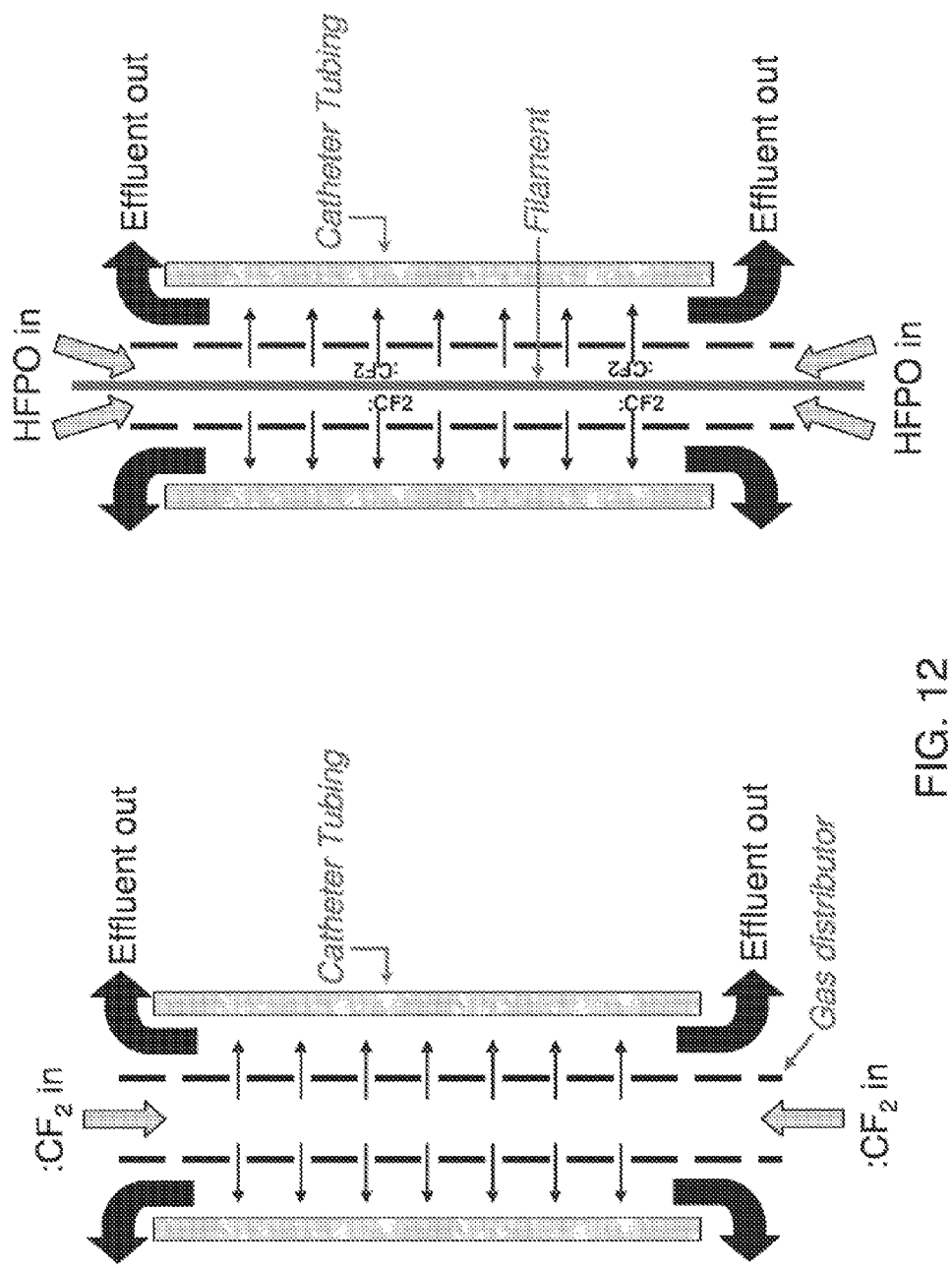
FIGS. 12, 13A and 13B illustrate different configurations for coating medical tubing according to embodiments

Other coated medical articles such as drug inhalers (e.g., metered-dose inhalers, dry powder inhalers) and medical tubing (e.g., a shunt or catheter used for transporting biological fluids and other materials) are disclosed herein, and may be coated using the methods described herein. When used as part of a heart-lung apparatus (e.g., a cardiopulmonary bypass pump), for example, the coated medical tubing disclosed herein may help prevent adverse immune (e.g., inflammatory) responses in the patient's body or clotting as a patient's blood passes through it. Reactive vapors (e.g., difluoroecrbene species) may be supplied to the medical tubing through a perforated tube. The tube may contain a metal filament, and the metal filament may be resistively-heated (FIG. 12). HFPO may be led into the tube, and may decompose (e.g., by pyrolysis) as it passes over the heated filament, creating difluorocarbene species. The difluorocarbene species may then form a fluorocarbon coating (e.g., PTFE) on the internal walls of the medical tubing. Alternatively, difluorocarbene species may be created elsewhere in the vacuum vessel, and then directed into the medical tubing using the tube so as to form a coating. For example, the difluorocarbene species may be drawn out of the tube (so as to form a coating on the medical tubing) by evacuating the medical tubing (FIG. 12). In another embodiment, the difluorocarbene species may be drawn into the medical tubing (so as to form a coating on the medical tubing) by evacuating the tube (FIG. 13a, b).

Figure 13B:
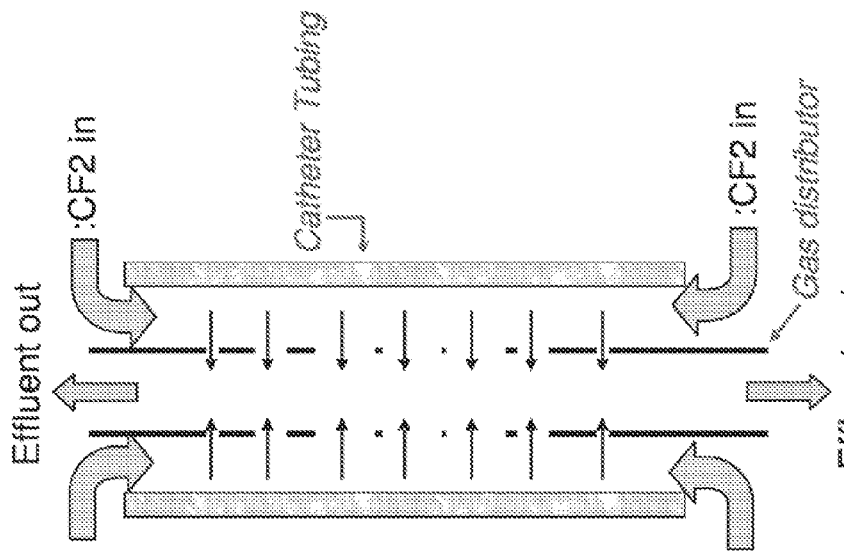
Figure 13A:
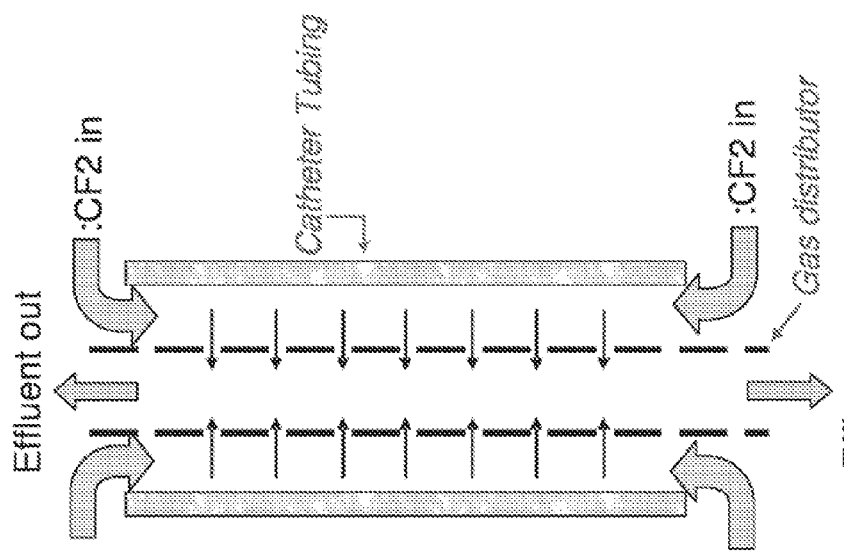

As described earlier, the tube may be perforated (FIGS. 12 and 13a, b), and the perforations may have different sizes (FIG. 13b). For example, portions of the tube that penetrate further into the lumen of the medical tubing (along the medical tubing's long axis) may have larger perforations than portions of the tube that remain near the medical tubing's open end. This may encourage reactive vapors that are directed into the medical tubing (e.g., by evacuating the tube) to cost the internal walls of the medical tubing more uniformly along the full length of the medical tubing.

Medical article seals may be coated by placing a substrate within a vacuum vessel, supporting the seals on pins protruding from the substrate, evacuating the vacuum vessel, adding a fluorocarbon vapor to the vacuum vessel, and forming a fluorocarbon coating on the seals.

Medical articles that can be coated using the methods described herein may be selected from the group consisting of syringe assemblies (including syringe barrels, plungers or pistons, and plunger seals or piston seals), drug cartridges, needleless injectors, liquid dispensing devices, liquid metering devices, metered dose inhalers and components thereof, dry powder inhalers and components thereof, catheters, and shunts, among others. It should be understood that various aspects of the methods described above can be combined so as to form desirable coatings on various medical articles. For example, a tube used to direct reactive vapors toward a medical article may be both perforated (as shown in FIG. 9) and notched (as shown in FIG. 10) or both tapered (as shown in FIG. 11) and notched. In another embodiment, a tube in the second zone of a vacuum vessel may be used to direct reactive vapors toward a medical article in a perforated plate, forming a coating on the medical article, after which the reactive vapors may be drawn into the first zone (see FIG. 2).

Example 1

Flow of Reactive Vapors Through Syringe Barrels

Figure 14:
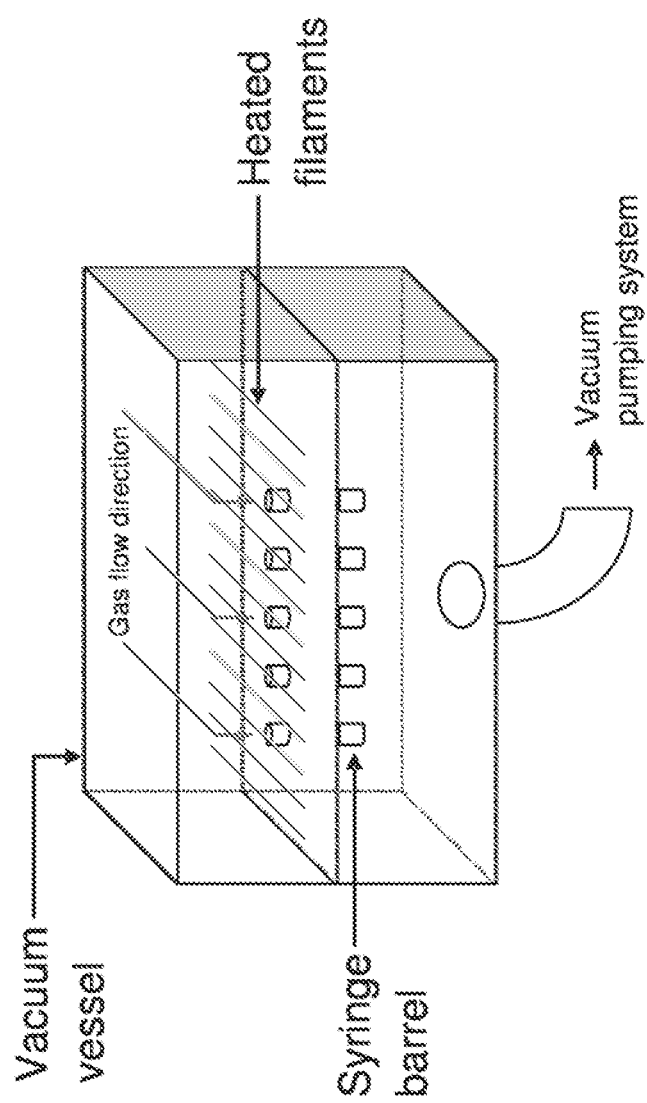
FIGS. 14-16 illustrate different configurations of systems for coating articles according to embodiments.

Syringe barrels with approximate dimensions of 0.25" internal diameter by 2" long were coated with PTFE using an iCVD coating system (FIG. 14). The coating system included a chamber (e.g., under vacuum) in which the syringe barrels were placed. To coat the inside of the syringe barrels, the coating system was set up to direct the reactive gas through the syringes by dividing it into two zones. This was done by placing the syringes in a cooled, perforated plate (to maintain the syringe temperature around 20° C. and prevent the syringes from heating up). The cooling plate used o-rings in the perforations to seal around the outside of the barrel of the syringes. The cooling plate was also sealed to the sides of the iCVD chamber to prevent gas leakage around the plate.

In the top zone of the chamber, the precursor gas was fed over an array of heated filaments. The top zone was maintained at the process pressure, ranging from 0.100 torr to 10 torr. The reactive gas flowed through the syringe barrels, depositing PTFE coating on the inside diameter. The bottom zone of the chamber was connected to the pumping system and was maintained at base pressure. The coating process was run for varying lengths of time to deposit PTFE coatings ranging from 0.1 to 10 microns in thickness.

103 plastic syringes were loaded into the cooling plate inside the iCVD coating system. The filament array was positioned approximately 1.5 cm above the cooling plate. The precursor gas was fed into the chamber through a gas distributor at a flow rate of 50 sccm. The pressure in the top zone stabilized at approximately 0.450 torr (with filament cold) while pressure in the bottom zone was about 0.060 torr. A power supply was used to resistively heat the filament array, using a voltage of about 70 to 75 V. The deposition was run for approximately 1 hour, resulting in a coating about 2 microns thick at the top of the syringe.

Example 2

Flow of Reactive Vapors Through Barrels and Bypass Holes

Figure 15:
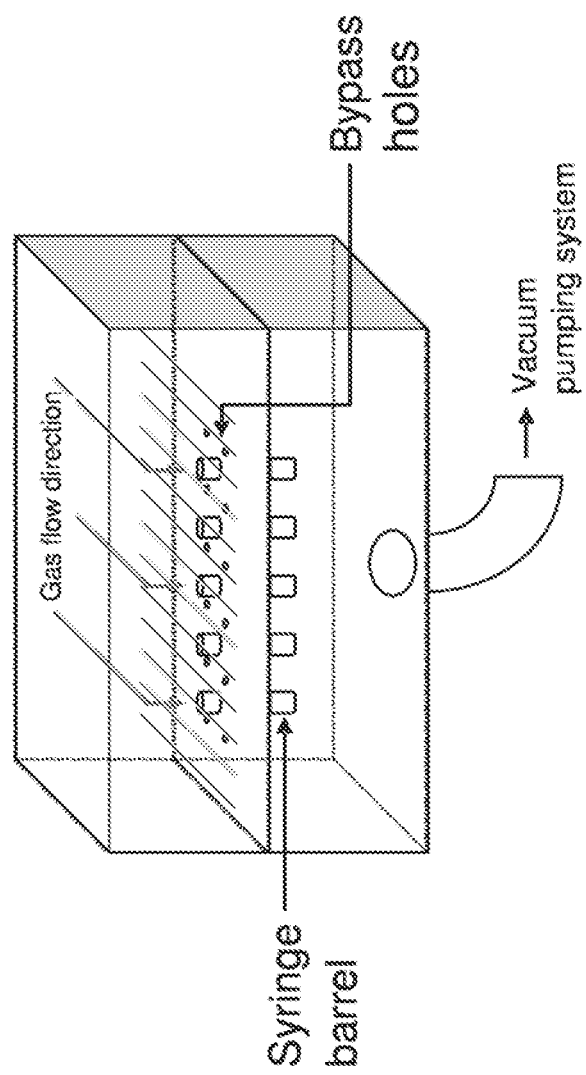

This Example is very similar to that used in Example 1, except that bypass holes were added to the cooling plate to allow a higher rate of precursor gas flow through the vacuum vessel (FIG. 15). These bypass holes were ideally smaller than the syringe inner diameter, but this was not a requirement.

10 plastic syringes were loaded into the cooling plate (with bypass holes) inside the iCVD coating system. The filament array was positioned approximately 1.5 cm above the cooling plate. The precursor gas was fed into the chamber through a gas distributor at a flow rate of 250 sccm. The pressure in the top zone stabilized at approximately 0.470 torr (with filament cold) while pressure in the bottom zone was at base pressure. A power supply was used to resistively heat the filament array, using a voltage of about 103 V. The deposition was run for approximately 46 minutes, resulting in a coating about 7 microns thick at the top of the syringe. The entire length of a syringe barrel with 2-mm inner diameter was coated.

Example 3

The Use of two Pumping Systems

Figure 16:
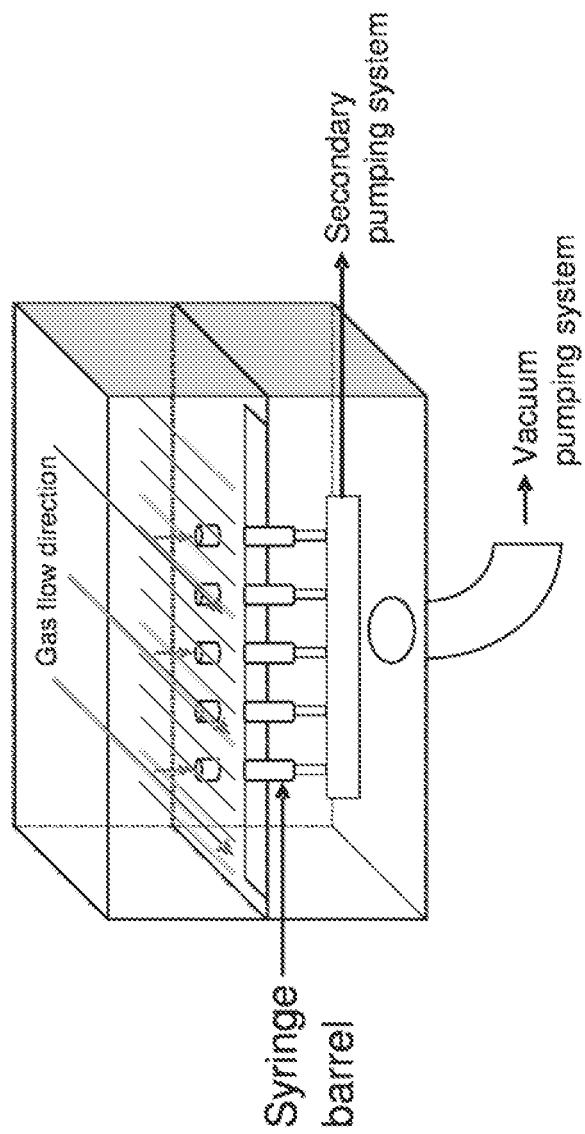

Two pumping systems were used to coat syringes. The first pumping system was attached to the chamber with an inline throttle valve to control the chamber pressure. This allowed a high flow rate through the chamber and pressure control that was independent of the syringe diameter. The second pumping system was attached directly to the syringes, effectively drawing the reactive gases down into the syringe barrels (FIG. 16). The second pumping system was attached to the barrels using different configurations, such as a manifold attaching individual tubes to each syringe or a manifold that sealed around the syringe barrels with a separate pump out port. This setup facilitated PTFE deposition at standard conditions, allowed the reactive gas to be independently drawn into the syringes.

Specifically, a cylindrical fixture was made to serve as a manifold for the syringes. This cylinder sealed at its bottom to the floor of the iCVD vacuum vessel. The top of the cylinder was sealed against a custom cooling plate. The cooling plate contained perforations with captured o-rings that sealed around each syringe barrel. The inside of the cylinder was evacuated through a port on the floor of the vacuum chamber. The rest of the chamber (above the syringes) was pumped out through a separate port on the vacuum chamber and pressure was controlled with a throttle valve.

103 plastic syringes were loaded into the cooling plate. The filament array was positioned approximately 1.5 cm above the cooling plate. The precursor gas was fed into the chamber through a gas distributor at a flow rate of 250 sccm. The pressure above the syringes was controlled with the throttle valve at a set point of 0.400 torr during deposition. The pressure in the cylinder was at base pressure. A power supply was used to resistively heat the filament array, using a voltage of about 103 V. The deposition was run for approximately 60 minutes, resulting in a coating about 8 microns thick at the top of the syringe. This method was also used to coat glass syringes with attached needles, yielding similar results.

Example 4

Coatings for Stoppers

Stoppers used in syringe barrels were coated with varying thicknesses of PTFE (50 nm to 2 μm) using the iCVD coating system. The stoppers were placed in the vacuum vessel either by sitting them on the cooling plate directly or using a plate configured with upright pins to hold the stoppers in place. On the pin plate, the stoppers were elevated slightly and spaced evenly across the plate. The pin plate then sat on the cooling plate. The filament array was positioned about 1.5 cm above the top of the stoppers. Precursor gas was fed into the chamber at a flow rate of 250 sccm. The chamber pressure was controlled at a setpoint of 0.200 torr using a throttle valve. The filament was heated using a power supply to a setpoint voltage of 103 V. The resulting PTFE coating thickness was measured during deposition using an interferometer. (A silicon wafer witness sample was coated along with the stoppers. The interferometer used a laser beam reflected off of the witness sample to monitor film thickness in real time.) This real time measurement was used for endpoint detection for each deposition.

Using this method, GVD has also produced stoppers coated with a base layer of iCVD silicone (siloxane-containing polymer) followed by an overcoat of PTFE.

We claim:

1. A medical article comprising:
   (a) a barrel and
   (b) a seal having an outer surface coated with a PTFE layer, wherein the PTFE layer is substantially free of surfactant and has a thickness of between about 1 nm and about 25 microns, and wherein at least a portion of the PTFE layer comprises polymeric chains formed of repeat units with at least 70% of the repeat units being $CF_2$,
   wherein the seal is constructed and arranged to move from a first position within the barrel to a second position within the barrel.

2. The medical article according to claim 1, wherein the medical article is selected from the group consisting of syringe assemblies, drug cartridges, needleless injectors, liquid dispensing devices, liquid metering devices, metered dose inhalers and components thereof, dry powder inhalers and components thereof, medical tubing, catheters, and shunts.

3. The medical article according to claim 1, wherein the barrel is a syringe barrel.

4. The medical article according to claim 1, wherein the outer surface of the seal is further coated with a siloxane-containing layer.

5. The medical article according to claim 4, wherein the siloxane-containing layer is formed on the outer surface of the seal and the PTFE layer is formed on the siloxane-containing layer.

6. The medical article according to claim 4, wherein the siloxane units are cyclic.

7. The medical article according to claim 4, wherein the siloxane-containing layer has a thickness ranging from about 1 nanometer to about 25 microns.

8. The medical article according to claim 7, wherein the siloxane-containing layer has a thickness ranging from about 5 nanometers to about 10 microns.

9. The medical article according to claim 7, wherein the siloxane-containing layer has a thickness ranging from about 25 nanometers to about 5 microns.

10. The medical article according to claim 1, wherein the PTFE layer has a thickness ranging from about 5 nanometers to about 10 microns.

11. The medical article according to claim 1, wherein the PTFE layer has a thickness ranging from about 25 nanometers to about 5 microns.

12. The medical article according to claim 1, wherein the seal is selected from the group consisting of a stopper, O-ring, plunger tip, and piston.

13. The medical article according to claim 1, wherein the seal is formed from rubber.

14. The medical article according to claim 1, wherein the seal is designed to slide in the barrel from the first position to the second position.

15. The medical article according to claim 1, wherein the seal is formed from thermoplastic elastomer or thermoplastic vulcanizate.

16. The medical article according to claim 15, wherein the seal is formed from styrene-butadiene copolymer.

17. The medical article according to claim 1, wherein the inner surface of the barrel is not coated with PTFE.

18. A medical article comprising
a seal having an outer surface coated with a PTFE layer, wherein the PTFE layer is substantially free of surfactant and has a thickness of between about 1 nm and about 25 microns, and wherein at least a portion of the PTFE layer comprises polymeric chains formed of repeat units with at least 70% of the repeat units being $CF_2$,
wherein the outer surface of the seal is further coated with a siloxane-containing layer.

* * * * *